US00PP12734P2

(12) United States Plant Patent
Vandenberg

(10) Patent No.: US PP12,734 P2
(45) Date of Patent: Jun. 25, 2002

(54) CHRYSANTHEMUM PLANT NAMED 'FICTION'

(75) Inventor: Cornelis P. Vandenberg, Salinas, CA (US)

(73) Assignee: Yoder Brothers, Inc., Barberton, OH (US)

( * ) Notice: Subject to any disclaimer, the term of this patent is extended or adjusted under 35 U.S.C. 154(b) by 11 days.

(21) Appl. No.: 09/757,512

(22) Filed: Jan. 11, 2001

(51) Int. Cl.[7] ..... A01H 5/00

(52) U.S. Cl. ..... Plt./286

(58) Field of Search ..... Plt./286

*Primary Examiner*—Howard J. Locker
(74) *Attorney, Agent, or Firm*—C. A. Whealy

(57) ABSTRACT

A distinct cultivar of Chrysanthemum plant named 'Fiction', characterized by its large daisy-type inflorescences that are about 7.4 cm; attractive purple and white bi-colored ray florets; very freely flowering habit with numerous inflorescences per stem; response time about 54 days; dark green foliage; strong stems; and excellent postproduction longevity with inflorescences maintaining good substance and color for more than four weeks in an interior environment.

2 Drawing Sheets

BACKGROUND OF THE INVENTION

The present invention relates to a new and distinct cultivar of Chrysanthemum plant, botanically known as *Chrysanthemum×morifolium* and hereinafter referred to by the name 'Fiction'.

The new Chrysanthemum is a product of a planned breeding program conducted by the Inventor in Salinas, Calif. and Alva, Fla. The objective of the breeding program is to create new cut Chrysanthemum cultivars having inflorescences with desirable colors and good form and substance.

The new Chrysanthemum originated from a cross made by the Inventor in July, 1995, in Salinas, Calif., of a proprietary Chrysanthemum seedling selection identified as code number D050, not patented, as the female, or seed, parent with a proprietary Chrysanthemum seedling selection identified as D497, not patented, as the male, or pollen, parent.

The cultivar Fiction was discovered and selected by the Inventor as a flowering plant within the progeny of the stated cross in a controlled environment in Alva, Fla., in November, 1996. The selection of this plant was based on its desirable inflorescence colors and good form and substance.

Asexual reproduction of the new Chrysanthemum by terminal cuttings taken in a controlled environment in Salinas, Calif., has shown that the unique features of this new Chrysanthemum are stable and reproduced true to type in successive generations.

SUMMARY OF THE INVENTION

The cultivar Fiction has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Fiction'. These characteristics in combination distinguish 'Fiction' as a new and distinct cultivar:

1. Large daisy-type inflorescences that are about 7.4 cm in diameter.
2. Attractive purple and white bi-colored ray florets.
3. Very freely flowering with numerous inflorescences per stem.
4. Response time about 54 days.
5. Dark green foliage.
6. Thick and strong stems.
7. Excellent postproduction longevity with inflorescences maintaining good substance and color for more than four weeks in an interior environment.

BRIEF DESCRIPTION OF THE PHOTOGRAPHS

The accompanying colored photographs illustrate the overall appearance of the new Chrysanthemum, showing the colors as true as it is reasonably possible to obtain in colored reproductions of this type. Colors in the photographs may differ slightly from the color values cited in the detailed botanical description which accurately describe the colors of the new Chrysanthemum.

The photograph on the first sheet comprises a side perspective view of a typical flowering stem of 'Fiction' grown as a spray-type cut Chrysanthemum.

The photograph on the second sheet comprises a close-up view of typical inflorescences of 'Fiction'.

DETAILED BOTANICAL DESCRIPTION

In the following description, color references are made to The Royal Horticultural Society Colour Chart except where general terms of ordinary dictionary significance are used. The following observations and measurements describe plants grown in Salinas, Calf., under conditions which approximate commercial practice in a double-layer polyethyene-covered greenhouse. Two-week old rooted cuttings were planted on Feb. 10, 2000 and received 18 long day/short nights followed by short day/long nights until flowering. Plants were grown as single-stem cut chrysanthemums. During the production time, the following environmental conditions were measured: day temperatures, 18 to 27° C.; night temperatures, 16 to 18° C.; and light levels, 2,000 to 4,000 foot-candles. Measurements and numerical values represent averages for six to ten typical flowering stems and were taken during the week of Apr. 30, 2000.

Botanical classification: *Chrysanthemum×morifolium* cultivar Fiction.

Commercial classification: Daisy spray-type cut Chrysanthemum.

Parentage:

*Female or seed parent.*—Proprietary *Chrysanthemum× morifolium* seedling selection identified as code number D050, not patented.

*Male or pollen parent.*—Proprietary *Chrysanthemum× morifolium* seedling selection identified as code number D497, not patented.

Propagation:

*Type.*—Terminal tip cuttings.

*Time to rooting.*—Seven to ten days with soil temperatures of 21° C.

*Root description.*—Fine, fibrous and well-branched.

Plant description:

*Appearance.*—Herbaceous daisy spray-type cut flower.

*Flowering stem description.*—Aspect: Erect Length: About 96.5 cm. Spray width: About 20.5 cm. Diameter: About 7 mm. Internode length: About 4.5 cm. Texture: Pubescent. Color: Close to 144A.

*Foliage description.*—Arrangement: Alternate. Length: About 9.8 cm. Width: About 7.1 cm. Apex: Cuspidate to mucronate. Base: Mostly truncate. Margin: Palmately lobed; sinuses mostly convergent and overlapping. Texture: Upper and lower surfaces pubescent; veins prominent on lower surface. Color: Young foliage upper surface: Much darker than 147A. Young foliage lower surface: Close to 147A. Mature foliage upper surface: Darker than 147A; venation, close to 147A to 147B. Mature foliage lower surface: Darker than 147B; venation, close to 147B. Petiole: Length: About 2.4 cm. Diameter: About 3 mm. Color: Close to 147B.

Flowering description:

*Appearance.*—Daisy spray-type inflorescence form with elongated oblong-shaped ray florets. Inflorescences borne on terminals, arising from leaf axils. Disc and ray florets arranged acropetally on a capitulum.

*Flowering response.*—Under natural conditions, plant flowers in the autumn/winter in the Northern Hemisphere. At other times of the year, inflorescence initiation and development can be induced under short day/long night conditions (at least 13.5 hours of darkness). Plants exposed to two or three weeks of long day/short night conditions after planting followed by photoinductive short day/long night conditions flower about 54 days later.

*Postproduction longevity.*—In an interior environment, flowering stems will maintain good color and substance for more than four weeks in an interior environment after one week of cool storage.

*Quantity of inflorescences.*—Freely flowering with about 15 inflorescences per flowering stem.

*Inflorescence size.*—Diameter: About 7.4 cm. Depth (height): About 1.4 cm. Diameter of disc: About 1.8 cm. Diameter of receptacle: About 6.5 mm.

*Ray florets.*—Shape: Elongated oblong. Length: About 4.1 cm. Width: About 1.1 cm. Apex: Rounded, mammilate or emarginate. Base: Attenuate. Margin: Entire. Texture: Satiny, smooth, glabrous; longitudinally ridged. Apspect: Concave. Aspect: Initially upright; when mature, about 80 to 85° from vertical. Number of ray florets per inflorescence: About 28 arranged in about two rows. Color: When opening and mature, upper surface: Apex, purple, 71A; midsection, alternating longitudinal purple and white streaks, 71A and 155D, respectfully; base, white, 155D. Purple color fading to 72A and white coloration becoming more dominant with subsequent development. When opening and mature, lower surface: Apex, purplish, 155D ground color underlain with close to 82A; midsection, alternating longitudinal purple and white streaks, 155D and faint 82A, respectfully; base, white, 155D.

*Disc florets.*—Shape: Tubular; slightly flared at apex. Length: About 6 mm. Width: Apex: About 1.5 mm. Base: About 1 mm. Number of disc florets per inflorescence: Numerous, about 178. Color: Immature: 144A. Mature: Apex: 7A. Mid-section: 144A. Base: 155D.

*Peduncle.*—Aspect: Strong, angled about 50 to 55° from vertical. Length: First peduncle: About 5.3 cm. Fourth peduncle: About 10.2 cm. Seventh peduncle: About 15.2 cm. Diameter: About 2.75 mm. Texture: Very fine pubescence. Color: 144A.

*Reproductive organs.*—Androecium: Present on disc florets only. Anther color: 13A. Amount of pollen: None observed to date. Gynoecium: Present on both ray and disc florets.

*Seed.*—Seed production has not been observed.

Disease resistance: Resistance to pathogens common to Chrysanthemums has not been observed on plants grown under commercial conditions.

Temperature tolerance: Plants of the new Chrysanthemum have demonstrated good tolerance to night temperatures as low as 5° C. and day temperatures lower than 40° C.

It is claimed:

1. A new and distinct cultivar of Chrysanthemum plant named 'Fiction', as illustrated and described.

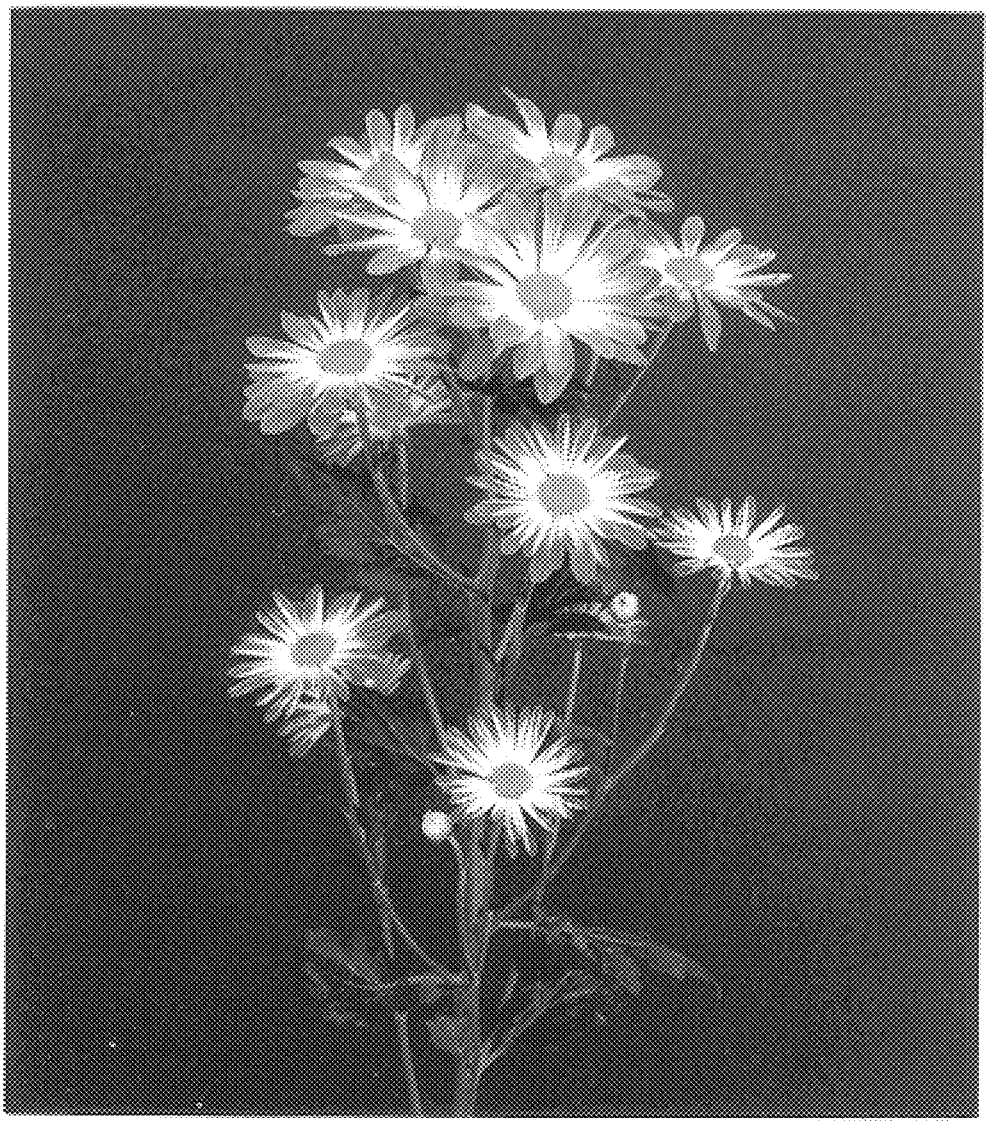

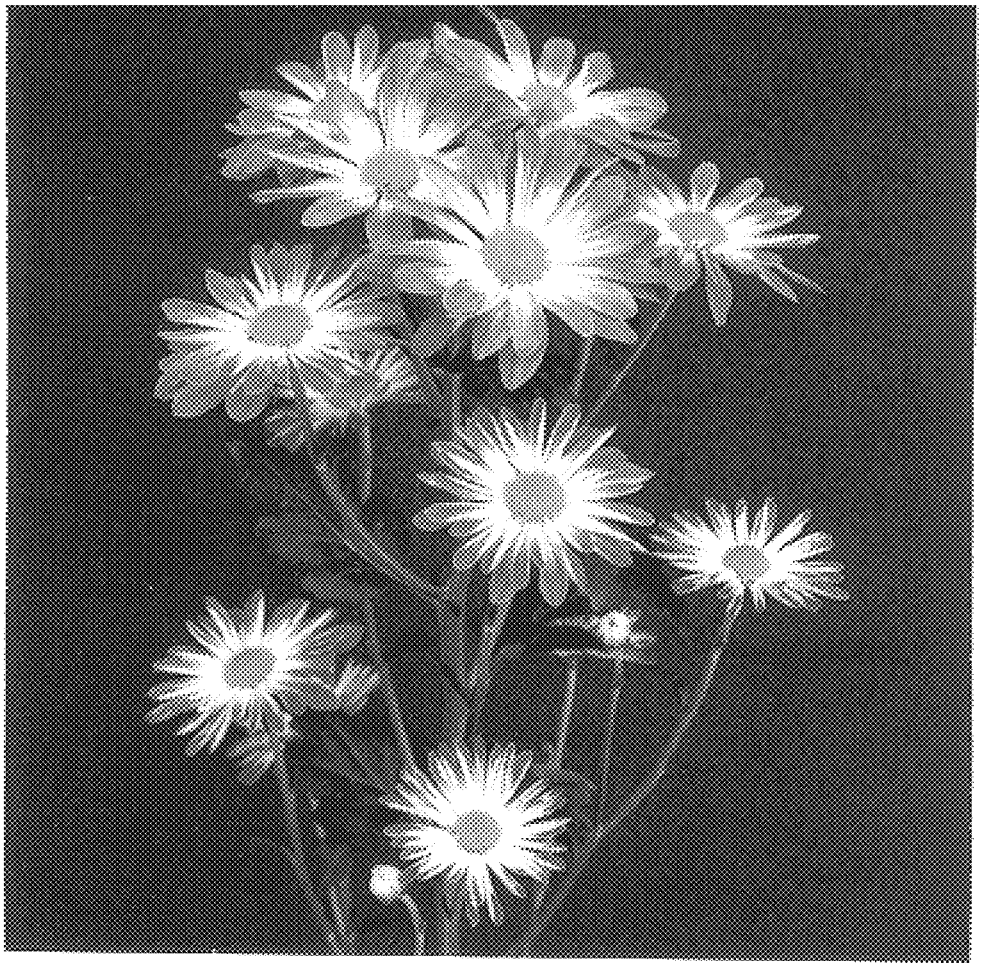

* * * * *